United States Patent
Camargo et al.

(10) Patent No.: US 11,952,891 B2
(45) Date of Patent: Apr. 9, 2024

(54) SYSTEMS AND METHOD FOR CONSTRAINING 3D FRACTURE MODEL PROPERTIES USING X-RAY MICRO-COMPUTED TOMOGRAPHY OF CORE PLUGS FOR NATURALLY FRACTURED RESERVOIRS

(71) Applicant: Saudi Arabian Oil Company, Dhahran (SA)

(72) Inventors: Otto Meza Camargo, Dhahran (SA); Karla Patricia Olvera Carranza, Dhahran (SA); Ivan Deshenenkov, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 17/892,476

(22) Filed: Aug. 22, 2022

(65) Prior Publication Data

US 2024/0060418 A1 Feb. 22, 2024

(51) Int. Cl.
*E21B 49/02* (2006.01)
*G01N 23/046* (2018.01)
(Continued)

(52) U.S. Cl.
CPC .......... *E21B 49/02* (2013.01); *G01N 23/046* (2013.01); *G01N 23/083* (2013.01); *G01N 33/24* (2013.01);
(Continued)

(58) Field of Classification Search
CPC ... E21B 49/02; E21B 2200/20; G01N 23/046; G01N 23/083; G01N 33/24;
(Continued)

(56) References Cited

U.S. PATENT DOCUMENTS 6,826,486 B1 * 11/2004 Malinverno .......... E21B 49/006
702/9
7,565,278 B2  7/2009 Li et al.
(Continued)

FOREIGN PATENT DOCUMENTS

AU  2021104861 A4  9/2021
CN  102339339 A  2/2012
(Continued)

OTHER PUBLICATIONS

Barton, Colleen A. et al.; "Fluid flow along potentially active faults in crystalline rock" Geology, Aug. 1995, v.23; No. 8; pp. 683-686.
(Continued)

*Primary Examiner* — Yong-Suk (Philip) Ro
(74) *Attorney, Agent, or Firm* — Bracewell LLP; Constance G. Rhebergen; Brian H. Tompkins

(57) ABSTRACT

The calibration of fracture models for naturally fractured reservoirs using fracture properties from X-ray micro-computed tomography (X-ray MicroCT). A core plug is obtained from a subsurface naturally fractured hydrocarbon reservoir, and a fracture property such as fracture porosity and a fracture effective permeability of the hydrocarbon reservoir are determined. A natural fracture model is generated using reservoir parameters and fluid flow paths, and fracture properties such as fracture porosity and a fracture effective permeability are determined from the natural fracture model. The fracture properties of the natural fracture model are calibrated using the fracture properties from the X-ray MicroCT analysis of the core plug.

20 Claims, 8 Drawing Sheets
(5 of 8 Drawing Sheet(s) Filed in Color)

(51) Int. Cl.
  *G01N 23/083* (2018.01)
  *G01N 33/24* (2006.01)
  *G01V 99/00* (2009.01)
(52) U.S. Cl.
  CPC ........ *G01V 99/005* (2013.01); *E21B 2200/20* (2020.05); *G01N 2223/04* (2013.01); *G01N 2223/419* (2013.01); *G01N 2223/616* (2013.01)
(58) Field of Classification Search
  CPC ......... G01N 2223/04; G01N 2223/419; G01N 2223/616; G01V 99/005
  See application file for complete search history.

(56) References Cited

U.S. PATENT DOCUMENTS

| | | | |
|---|---|---|---|
| 8,081,796 | B2 | 12/2011 | Derzhi et al. |
| 8,938,045 | B2 | 1/2015 | Dvorkin et al. |
| 10,572,611 | B2 | 2/2020 | Huang et al. |
| 10,607,043 | B2 | 3/2020 | Camargo et al. |
| 11,530,555 | B2* | 12/2022 | Perreau ................. A43C 19/00 |
| 11,578,596 | B2* | 2/2023 | Camargo ................. E21B 47/06 |
| 2007/0272407 | A1* | 11/2007 | Lehman ................. E21B 49/00 166/308.1 |
| 2009/0274276 | A1* | 11/2009 | Wraight ................. H05G 1/10 378/101 |
| 2012/0221306 | A1 | 8/2012 | Hurley et al. |
| 2017/0051598 | A1 | 2/2017 | Ouenes |
| 2017/0176228 | A1* | 6/2017 | Elisabeth ................. E21B 21/08 |
| 2017/0275970 | A1 | 9/2017 | Crawford et al. |
| 2019/0080122 | A1* | 3/2019 | Camargo ................. G06G 7/48 |
| 2019/0227087 | A1 | 7/2019 | Belani et al. |
| 2020/0095858 | A1 | 3/2020 | Bouaouaja et al. |

FOREIGN PATENT DOCUMENTS

| | | |
|---|---|---|
| CN | 103822865 A | 5/2014 |
| CN | 104730596 A | 6/2015 |
| CN | 105279790 A | 1/2016 |
| CN | 106019405 A | 10/2016 |
| CN | 107240154 A | 10/2017 |
| CN | 109887083 A | 6/2019 |
| CN | 110853138 A | 2/2020 |
| CN | 114379092 A | 4/2022 |

OTHER PUBLICATIONS

Voorn, Maarten et al.; "Porosity, permeability and 3D fracture network characterisation of dolomite reservoir rock samples" J Pet Sci Eng. Mar. 1, 2015; 127(March); pp. 270-285.

Cai, Yidong et al.; "Permeability evolution in fractured coal—Combining triaxial confinement with X-ray computed tomography, acoustic emission and ultrasonic techniques" International Journal of Coal Geology 122 (2014); pp. 91-104.

International Search Report and Written Opinion issued in International Application No. PCT/US2023/030840, report dated Nov. 24, 2023; pp. 1-17.

Watanabe, Noraki et al.; "X-ray based numerical analysis of fracture flow for core samples under various confining pressures" Engineering Geology 123 (2011); pp. 338-346.

* cited by examiner

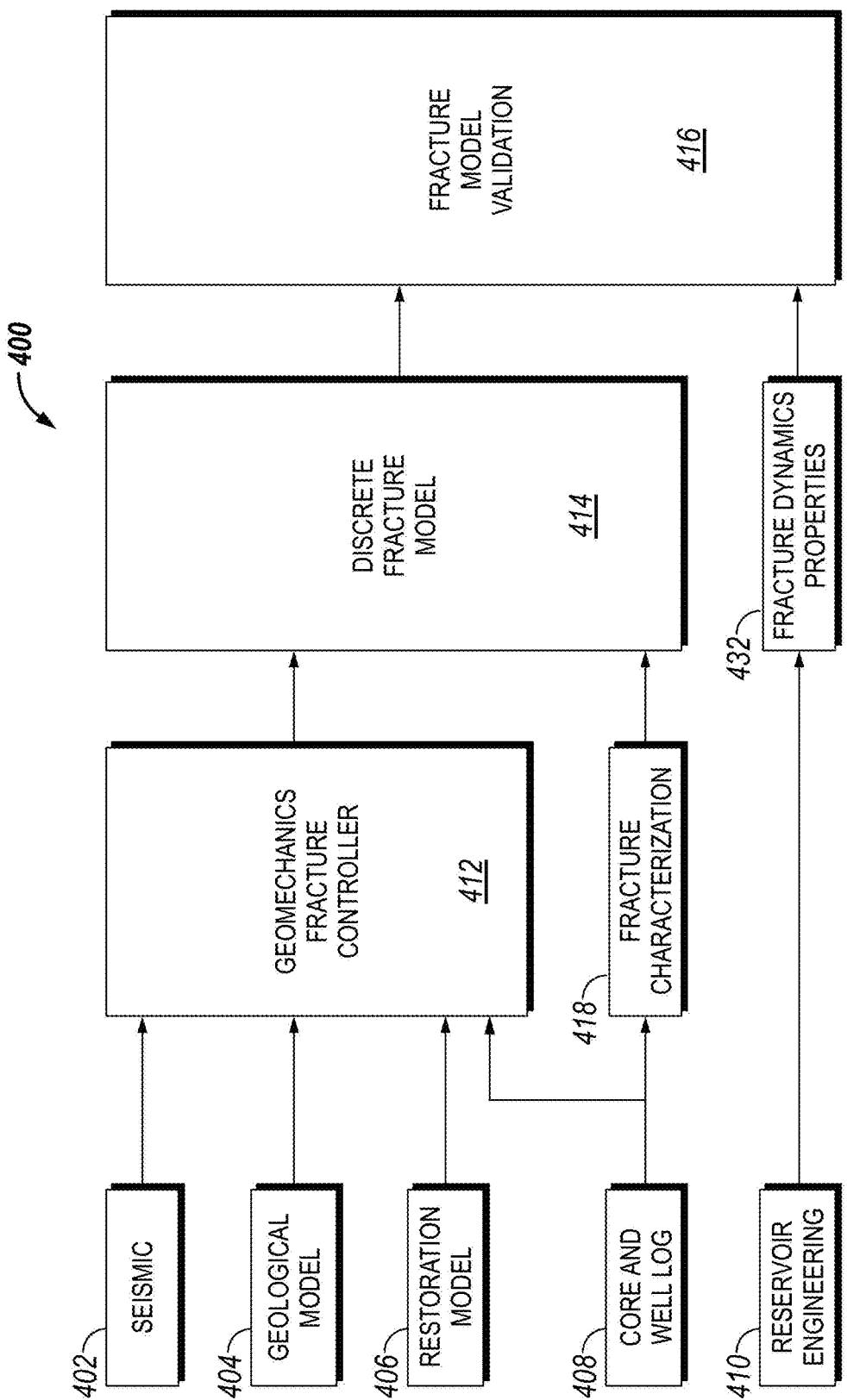

SAMPLE_#41

SYSTEMS AND METHOD FOR CONSTRAINING 3D FRACTURE MODEL PROPERTIES USING X-RAY MICRO-COMPUTED TOMOGRAPHY OF CORE PLUGS FOR NATURALLY FRACTURED RESERVOIRS

BACKGROUND

Field of the Disclosure

The present disclosure generally relates to forming models of subsurface reservoirs and estimating natural fracture distribution and properties. More specifically, embodiments of the disclosure relate to using X-ray micro-computed tomography to constrain properties of such fracture models.

Description of the Related Art

Natural fractures present in subsurface formations are discontinuities representing a surface or zone of mechanical failure in the formation. Natural fractures have been formed over geological time as a result of movements and deformations within the subsurface rock over time. Natural fractures continue to be formed as a result of microseismic events which are slight tremors or movements in the earth's crust arising from various natural sources. Natural fractures are thus different in origin and nature from fractures induced in earth formations from the practice of hydraulic fracturing or fracking.

Fracture distributions are related to various factors such as intrinsic rock mechanics properties, as well as movements and deformation of the formation rock layers due to different tectonic stages to which the lithological formations are subjected through geological time. However, those parameters are usually unknown for the purposes of hydrocarbon exploration and development. Thus, the presence of natural fractures must be modeled to understand the most probable or likely fracture distribution.

SUMMARY

Naturally fractured reservoirs are usually represented numerically by discrete elements distributed stochastically within a 3D grid geological model. In such models, those discrete elements (or planes) are converted to grid model in order to determine a dual-porosity/dual-permeability model. To further produce a set of fracture properties such as a fracture permeability tensor and fracture porosity, further calibration may be performed. Typical approaches include a static calibration between matrix permeability and fracture permeability.

Embodiments of the disclosure are directed to the use of X-ray micro-computed tomography (also referred to as "X-ray microtomography," "MicroCT," or "μCT") to evaluate different features of the rock fabric and, more particularly, to determine natural fractures properties that may be used to constrain a fracture model.

In some embodiments, a method of drilling a well in a subsurface geological structure to a location in a subsurface hydrocarbon reservoir indicated by a natural fracture network model of the reservoir is provided. The method includes obtaining a core plug from the subsurface geological structure, obtaining an image of a sample from the core plug using X-ray micro-computed tomography, and determining, using the image, a first fracture porosity and a first fracture effective permeability of the subsurface hydrocarbon reservoir. The method also includes obtaining reservoir parameters representing properties of the subsurface reservoir for processing in a data processing system, forming a natural fracture model by processing the obtained reservoir parameters to identify the presence and extent of natural fractures at locations in the subsurface hydrocarbon reservoir, and identifying a fluid flow path using a shear stress, a normal stress, and an aperture of a fracture. Additionally, the method includes determining a discrete natural fracture network in the natural fracture model using the fluid flow path, and determining a second fracture porosity and a second fracture effective permeability from the nature fracture model. The method further includes comparing the second fracture porosity to the first fracture porosity and the second fracture effective permeability to the first fracture effective permeability and calibrating the natural fracture model based on the comparison. The method also includes drilling a well in the subsurface geological structure to a location in the subsurface hydrocarbon reservoir based on the identified presence and extent of natural fractures from the natural fracture model.

In some embodiments, the reservoir parameters include seismic attributes from seismic surveys of the subsurface geological structure. In some embodiments, the reservoir parameters include rock and mechanical properties from geological models of the subsurface geological structure. In some embodiments, the reservoir parameters include structural restoration models of the subsurface geological structure. In some embodiments, the reservoir parameters include rock geological characterizations of the subsurface geological structure. In some embodiments, the reservoir parameters include reservoir engineering measures obtained from production from the subsurface hydrocarbon reservoir. In some embodiments, obtaining an image of a sample from the core plug using X-ray micro-computed tomography includes obtaining a sub-sample of the sample of the core plug and obtaining an image of the sub-sample at a greater resolution than the image of the sample. In some embodiments, the method includes determining, using the image, a fracture aperture of the subsurface hydrocarbon reservoir. In some embodiments, determining a second fracture porosity and a second fracture effective permeability from the nature fracture model comprises converting a discrete fracture plane of the natural fracture model to a grid model.

In another embodiment, a non-transitory computer-readable storage medium having executable code stored thereon of drilling a well in a subsurface geological structure to a location in a subsurface hydrocarbon reservoir indicated by a natural fracture network model of the reservoir. The executable code comprising a set of instructions that causes a processor to perform operations that include obtaining a core plug from the subsurface geological structure, obtaining an image of a sample from the core plug using X-ray micro-computed tomography, and determining, using the image, a first fracture porosity and a first fracture effective permeability of the subsurface hydrocarbon reservoir. The operations also include obtaining reservoir parameters representing properties of the subsurface reservoir for processing in a data processing system, forming a natural fracture model by processing the obtained reservoir parameters to identify the presence and extent of natural fractures at locations in the subsurface hydrocarbon reservoir, and identifying a fluid flow path using a shear stress, a normal stress, and an aperture of a fracture. Additionally, the operations include determining a discrete natural fracture network in the natural fracture model using the fluid flow path, and determining a second fracture porosity and a second fracture effective permeability from the nature fracture model. The operations further include comparing the second fracture porosity to the first fracture porosity and the second fracture effective permeability to the first fracture effective permeability and calibrating the natural fracture model based on the comparison. The operations also include drilling a well in the subsurface geological structure to a location in the subsurface hydrocarbon reservoir based on the identified presence and extent of natural fractures from the natural fracture model.

In some embodiments, the reservoir parameters include seismic attributes from seismic surveys of the subsurface geological structure. In some embodiments, the reservoir parameters include rock and mechanical properties from geological models of the subsurface geological structure. In some embodiments, the reservoir parameters include structural restoration models of the subsurface geological structure. In some embodiments, the reservoir parameters include rock geological characterizations of the subsurface geological structure. In some embodiments, the reservoir parameters include reservoir engineering measures obtained from production from the subsurface hydrocarbon reservoir. In some embodiments, obtaining an image of a sample from the core plug using X-ray micro-computed tomography includes obtaining a sub-sample of the sample of the core plug and obtaining an image of the sub-sample at a greater resolution than the image of the sample. In some embodiments, the method includes determining, using the image, a fracture aperture of the subsurface hydrocarbon reservoir. In some embodiments, determining a second fracture porosity and a second fracture effective permeability from the nature fracture model comprises converting a discrete fracture plane of the natural fracture model to a grid model.

In another embodiment, a system of drilling a well in a subsurface geological structure to a location in a subsurface hydrocarbon reservoir indicated by a natural fracture network model of the reservoir. The system includes a processor and a non-transitory computer-readable memory accessible by the processor and having executable code stored thereon. The executable code comprising a set of instructions that causes a processor to perform operations that include obtaining a core plug from the subsurface geological structure, obtaining an image of a sample from the core plug using X-ray micro-computed tomography, and determining, using the image, a first fracture porosity and a first fracture effective permeability of the subsurface hydrocarbon reservoir. The operations also include obtaining reservoir parameters representing properties of the subsurface reservoir for processing in a data processing system, forming a natural fracture model by processing the obtained reservoir parameters to identify the presence and extent of natural fractures at locations in the subsurface hydrocarbon reservoir, and identifying a fluid flow path using a shear stress, a normal stress, and an aperture of a fracture. Additionally, the operations include determining a discrete natural fracture network in the natural fracture model using the fluid flow path, and determining a second fracture porosity and a second fracture effective permeability from the nature fracture model. The operations further include comparing the second fracture porosity to the first fracture porosity and the second fracture effective permeability to the first fracture effective permeability and calibrating the natural fracture model based on the comparison. The operations also include drilling a well in the subsurface geological structure to a location in the subsurface hydrocarbon reservoir based on the identified presence and extent of natural fractures from the natural fracture model.

In some embodiments, the reservoir parameters include seismic attributes from seismic surveys of the subsurface geological structure. In some embodiments, the reservoir parameters include rock and mechanical properties from geological models of the subsurface geological structure. In some embodiments, the reservoir parameters include structural restoration models of the subsurface geological structure. In some embodiments, the reservoir parameters include rock geological characterizations of the subsurface geological structure. In some embodiments, the reservoir parameters include reservoir engineering measures obtained from production from the subsurface hydrocarbon reservoir. In some embodiments, obtaining an image of a sample from the core plug using X-ray micro-computed tomography includes obtaining a sub-sample of the sample of the core plug and obtaining an image of the sub-sample at a greater resolution than the image of the sample. In some embodiments, the operations include determining, using the image, a fracture aperture of the subsurface hydrocarbon reservoir. In some embodiments, determining a second fracture porosity and a second fracture effective permeability from the nature fracture model comprises converting a discrete fracture plane of the natural fracture model to a grid model.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 4A and 4B are flowcharts of a process for determining a discrete natural fracture distribution of a 3D fracture model in accordance with an embodiment of the disclosure;

DETAILED DESCRIPTION

The present disclosure will be described more fully with reference to the accompanying drawings, which illustrate embodiments of the disclosure. This disclosure may, however, be embodied in many different forms and should not be construed as limited to the illustrated embodiments. Rather, these embodiments are provided so that this disclosure will be thorough and complete, and will fully convey the scope of the disclosure to those skilled in the art.

Embodiments of the disclosure are directed to the calibration of fracture models for naturally fractured reservoirs using fracture properties from X-ray MicroCT. The X-ray MicroCT may be used to evaluate different features of the rock fabric of a core plug, such as by identifying natural fractures and their properties at micron (that is, micrometer) scale. In some embodiments, the X-ray MicroCT may generate digital tomographies of target core plugs with macro magnification (that is, a resolution of about 10 microns to about 20 microns) for a 1.5" core plug and 4× and 20× magnification (a resolution of about 0.5 to about 10 microns resolution) for the sub-samples of a core plug.

Figure 1:
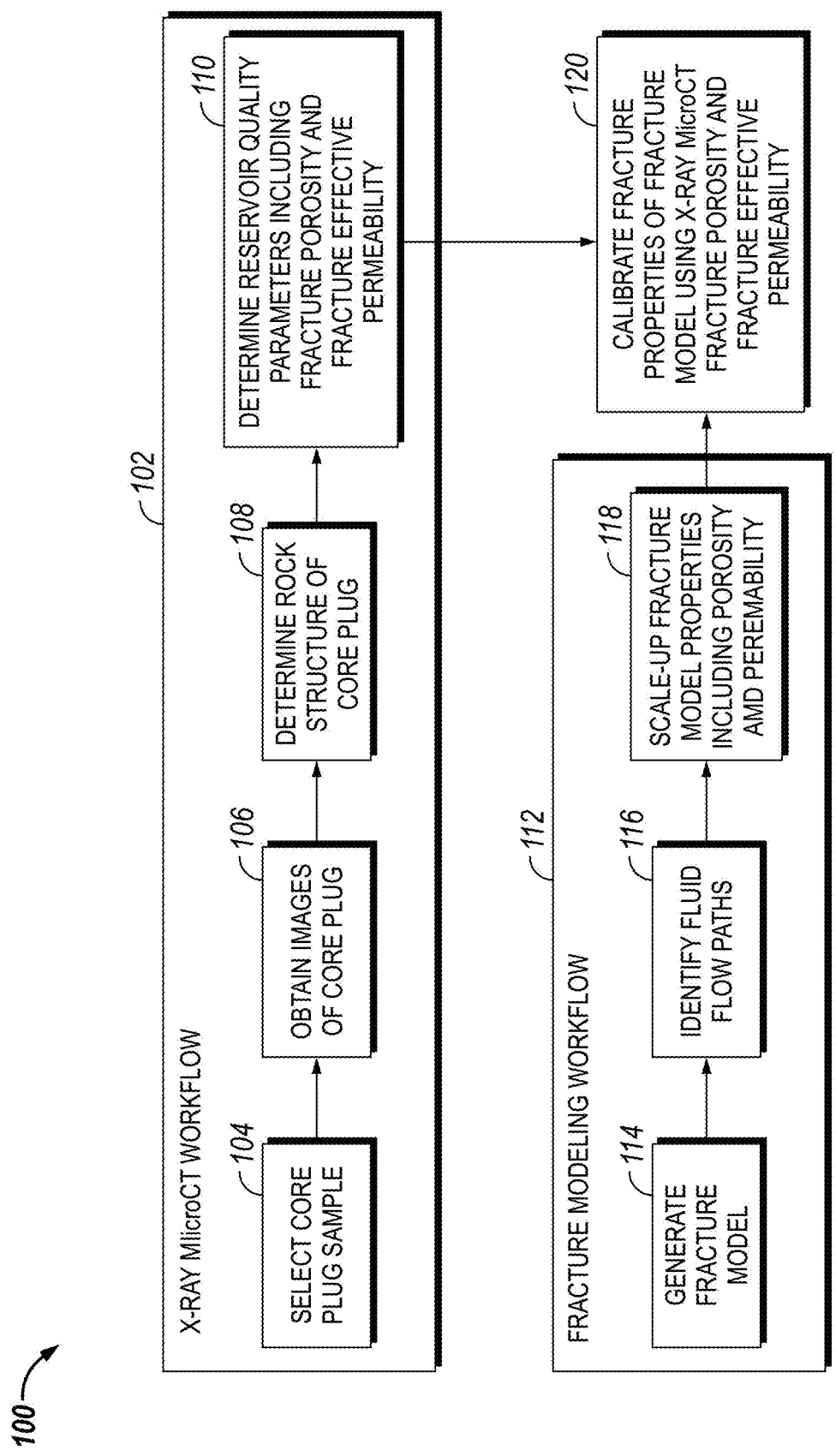
FIG. 1 is a flowchart of a process for the calibration of fracture models using fracture properties from X-ray MicroCT in accordance with an embodiment of the disclosure.

FIG. 1 depicts a process 100 for the calibration of fracture models using fracture properties from X-ray MicroCT in accordance with an embodiment of the disclosure. FIG. 1 depicts an X-ray MicroCT workflow 102 that includes core plug sample selection (block 104), obtaining X-ray MicroCT images of the core plug (block 106), identification of the rock structure (block 108) and determination of reservoir quality parameters that includes fracture porosity and fracture permeability (block 110).

FIG. 1 also depicts a fracture modeling workflow 112 that includes generating a fracture model (block 114), identifying fluid flow paths (block 116), and scaling up fracture properties such as fracture porosity, and permeability (block 118). The fracture properties of the fracture model may then be calibrated using the fracture properties from the X-ray MicroCT workflow 102.

Initially, core plug samples may be selected (block 104) from a core plug. In some embodiments, core plug samples may be selected based core descriptions, thin-section petrography, scanning electron microscope (SEM), or any combination thereof, such as described in M. Dernaika 2018. Core descriptions may include, for example, sedimentological descriptions that use whole core and well logging data. For example, samples having visual fractures and possible internal fractures (for example, as identified from borehole imagery data) may be selected from a whole core sample. Additionally, various samples may be obtained from a naturally fractured reservoir of interest. For example, sampling locations may be identified to represent variations in lithofacies, texture, and porosity type.

Next, images of the core plug samples may be obtained using X-ray MicroCT (block 104). Obtaining images may include pore and grain segmentation and identification of pore structures (for example, intergranular pores and fractures). Obtaining images of the core plug samples may also include the selection of smaller sub-volumes for greater resolution imaging and analysis. In such embodiments, the sub-volume samples may be imaged at a resolution of 4 micrometers (μm) to identify the matrix to fracture interface to study morphology and properties of fractures. Such imaging may enable the evaluation of the rock structure at multiple scales (also referred to as "multi-scale"), resulting in an improved evaluation of the impact of rock quality and geological heterogeneity on the permeability of the rocks from the reservoir of interest.

The multi-scale digital rock analysis provides varying resolution and a systematic procedure for coarsening and refinement. In some embodiments, Darcy's model may be used to approximate pressure and fluxes on a coarse grid in large-scale discontinuities, whereas fine-scale effects may be captured through basis functions computed numerically by solving local Stokes-Brinkman flow problems on the underlying fine-scale geocellular grid. The Stokes-Brinkman equations may provide a unified approach to simulating free-flow and porous regions using a single system of equations while avoid explicit interface modeling and reducing to Darcy or Stokes flow in certain parameter limits. In such embodiments, the fine-scale flow in pore networks may be represented within a coarse-scale Darcy-flow model in fractured elements.

Next, the rock structure in core plug samples may be identified (block 108). In some embodiments, numerical modeling of permeability in fractures may be performed at the largest magnification tomography of 4 μm resolution. 3D images may be then segmented to allow porosity and permeability computation at sub-volume scales. The identification of the rock structure may include the identification of two main phases: pores and grains.

As will be appreciated, incompressible flow in a porous rock matrix typically obeys Darcy's law and may be described by a first-order elliptic system in which Darcy's law was combined with a mass-conservation equation to relate the pressure and the total (interstitial) velocity. In contrast, incompressible flow in open domains obeys the Stokes equations. As known in the art, the Stokes-Brinkman equations combine Darcy and Stokes models into a single equation. This Stokes-Brinkman model may provide a unified approach to model flow in both the fractures and the intergranular porous subdomains using a single system of equations. In the free-flow (or fluid) domain, the permeability may be assumed to tend to infinity and the effective viscosity may be assumed to equal to the fluid viscosity (without these assumptions the modeling transforms into the coupled Darcy-Stokes equations which reintroduce the requirement for interface conditions and computational intractability).

Figure 2:
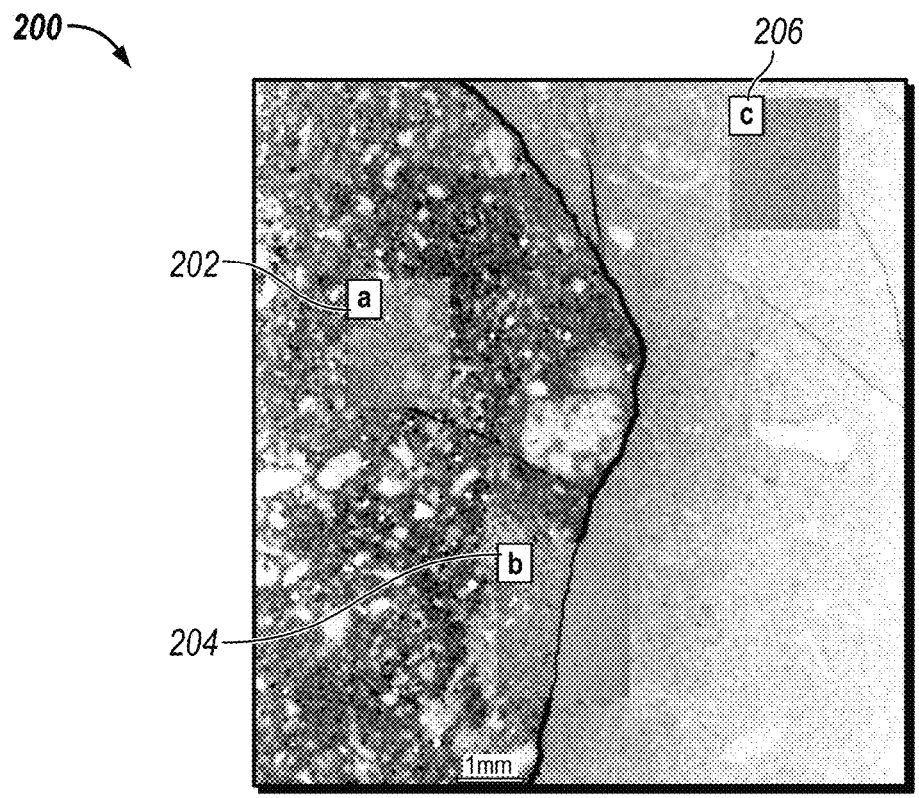
FIG. 2 is a CT image showing three sub-samples were selected to characterize the matrix system under high-resolution CT imaging in accordance with an embodiment of the disclosure.

Reservoir quality parameters such as fracture porosity and fracture permeability may then be determined from the X-ray MicroCT workflow (block 118). In some embodiments, the parameters may include fracture aperture. In some embodiments, effective permeability on coarser grids may be determined using a flow-based upscaling procedure based on the Stokes-Brinkman equation. To build the coarser grid, the permeability of unresolved porous materials within the grid may be estimated. In some embodiments, the permeability of unresolved porous materials may be estimated using three sub-samples. By way of example, FIG. 2 is a CT image 200 showing three sub-samples were selected to characterize the matrix system under high-resolution CT imaging. The sub-samples include a first rock type 202 (porous rock), a rock type interface 204, and a second rock type 206 (tight rock).

Figure 3:
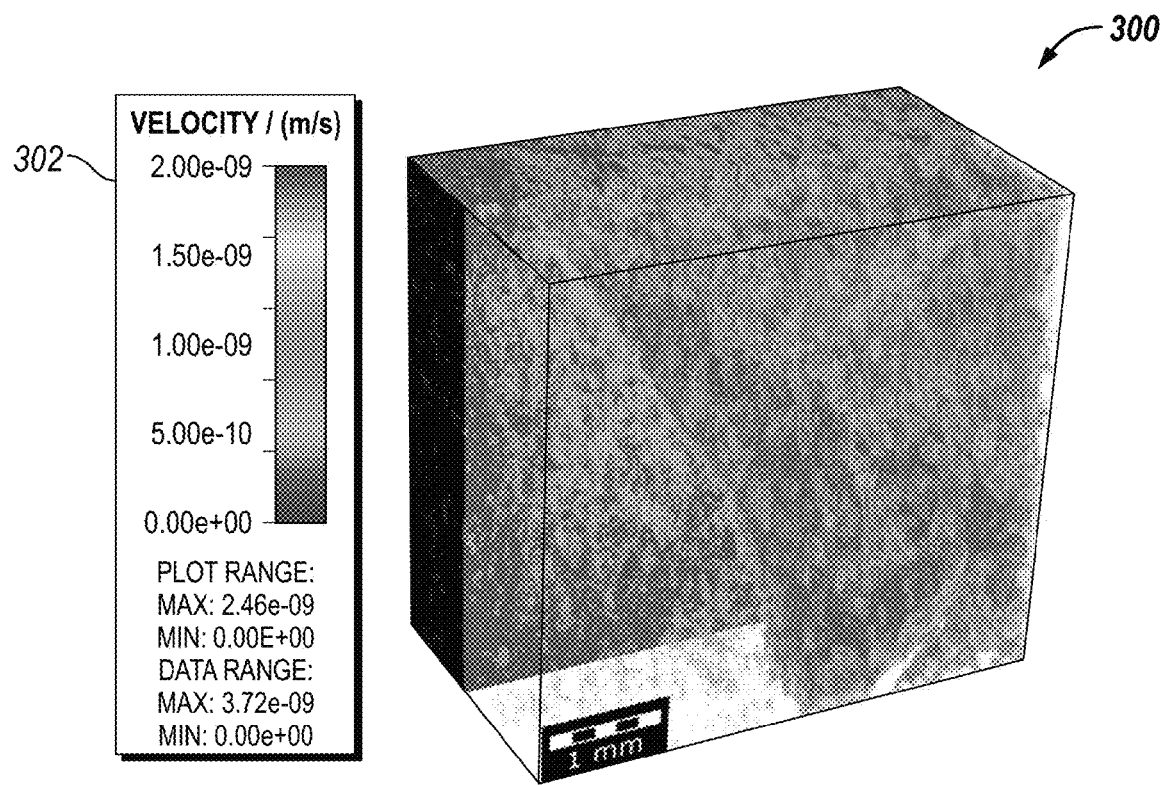
FIG. 3 is an image of a velocity field 3 in a fractured core plug sample in accordance with an embodiment of the disclosure.

The modeling may result in permeability enhancement and porosity-permeability relations in the fractured system in three orthogonal directions. As will be appreciated, the interaction of the intergranular system with the fracture network may contribute to the bulk enhancement of flow between dead-end pores and improves permeability of the system by two orders of magnitude in comparison with the intergranular pores. By way of example, FIG. 3 depicts a velocity field 300 in a fractured core plug sample in accordance with an embodiment of the disclosure. FIG. 3 includes a color legend 302 identifying the velocity in meters/second (m/s) by color. As shown in FIG. 3 the fracture connects porous rock fabrics and tight rock fabrics, and provides a fluid conduit. In some embodiments, the results can be used for the permeability anisotropy prediction based on fractures properties derived from core or well log data analysis to improve permeability simulation in the grid of geological models.

The process of FIG. 1 also includes the fracture modeling workflow 112, which may include distributing fractures using stochastics algorithms as well as building tectonic deformation model and brittleness index. Initially, a fracture model may be generated using a paleo-structural reconstruction deformation model to identify tectonic events that originate natural factures. As will be appreciated, various techniques may be used to build a paleo-structural reconstruction deformation model and capture the tectonic deformation in a region of geological setting, such as elasticity, spring algorithm, boundary element methods, volume-based deformation, and finite element methods.

Such 3D deformation algorithms may be based on several simulation techniques, which solve strains and stresses related mainly to the major stage of tectonic deformation (i.e., Kine3D™ available from Aspen Technology, Inc. of Bedford, Massachusetts, U.S.A., or the Move suite available from Petroleum Experts LTD of Edinburgh, Scotland, United Kingdom). The resultant tectonic drivers may be used as an input to predict spatial distribution and intensity variability of a fracture network. The structural setting and tectonic evolution may inform the selection of the 3D paleo-structural reconstruction deformation technique.

Moreover, advance 3D seismic discontinuity attributes such as Tensor/SO-semblance/Dip may contribute to identify possible lineaments variations in terms of orientations, which may indicate a significant impact of faulting or folding deformation within an area. Clustering seismic discontinuity analysis may be used to identify variations or anomalies that can provide insights in the complexity of a network at seismic resolution scale.

Mechanical properties may be modeled using different algorithms such as Sequential Gaussian Simulation to represent the elastic and rock strength properties. The first stage of the 3D stress analysis may include calculating stresses that represent the pre-production conditions throughout the reservoir and its surroundings. In such embodiments, the stress equilibrium may be solved numerically due to the complex variation of structure and properties within the model. Geomechanical simulation software typically uses a finite element method to determine the required solution, producing a 3D stress tensor magnitudes and orientations that vary both laterally and vertically. The fracture model uses the structure and the rock mechanical properties defined in the preceding sections together with the loads that govern stresses (gravitational, pore pressures and boundary conditions) in order to simulate the initial stress state of the field.

Elastic and strength properties as well as stress magnitudes may be used as inputs to compute 3D discrete geomechanical facies which represent mechanical units within the reservoir with differential response to the stress/strain deformation.

Thus, the determination of a natural fracture distribution of a 3D fracture model using geomechanics may use rock mechanical properties combined with additional data like seismic, structural restoration and geomechanics determine the natural fractures. In some embodiments, the determination of a 3D fracture model and a natural fracture distribution may be performed according to the techniques described in U.S. Pat. No. 10,607,043 filed Sep. 14, 2017, and titled "SUBSURFACE RESERVOIR MODEL WITH 3D NATURAL FRACTURES PREDICTION," a copy of which is incorporated by reference in its entirety.

Figure 4B:
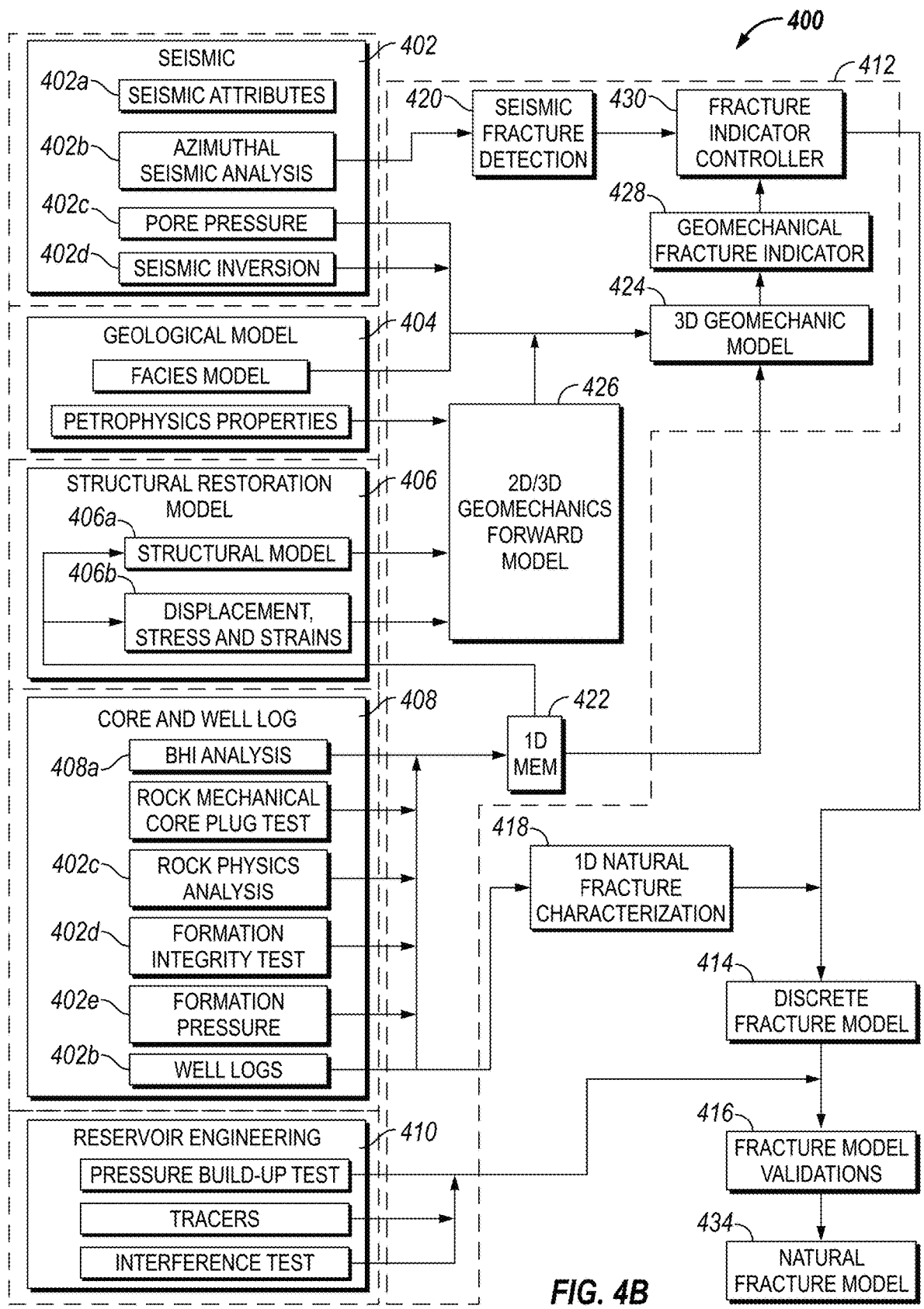

FIGS. 4A and 4B depict a process 400 for determining a natural fracture distribution of a 3D fracture model in accordance with an embodiment of the disclosure. The inputs to the process 400 may include different reservoir parameters and properties obtained via different techniques and known earth science. As shown in FIGS. 4A and 4B, such inputs may include seismic attributes from seismic surveys (402); rock and mechanical properties from geological modeling (404); measures from structural restoration models (406); core and well logs (408) obtained from formation core samples and well logs performed in wellbores drilling into a reservoir; and reservoir engineering measures obtained (410) from production measures and reservoir simulations of a reservoir layer.

The process 400 may include a geomechanics fracture controller (412), determining a discrete fracture model (414), and validating the fracture model (416). The geomechanics fracture controller (412) may integrate the paleo-stress from structural restoration model (406) obtained for several stages in geological time, and current stress regime conditions obtained through a geomechanical numerical simulation model. In some embodiments, geomechanics fracture controller (412) may apply seismic volume interpretation techniques and attributes to detect possible faults and natural fractures alignments by using post stack discontinuities attributes, azimuthal analysis, and elastic seismic inversion.

The determination of the natural fracture model (414) may include quantifying fracture density in the subsurface reservoir layer using the output from the geomechanics fracture controller (412), and a 1D fracture characterization (418) provided from core samples and borehole well log images from a borehole image (BHI) analysis process 408a (shown in FIG. 4B). The determination of the natural fracture model (414) also includes the determination of fracture dimensions and their properties into the discrete fracture model, described in the disclosure. Examples of the fracture properties resulting from the determination of the natural fracture model (414) include fracture position, orientation, geometry, porosity, aperture, permeability, and the like. In other embodiments, other fracture properties may also be estimated during the determination of the natural fracture model (414).

The validation of the fracture model (416) may include cross-checking or validating the model using reservoir production data. In some embodiments, the natural fracture model may be upscaled to conform to a fine-scale cell grid of geological model and reproduce the natural fracture distribution and their properties, for comparison with the reservoir production data for validation proposes. Several types of reservoir production data can be used to calibrate the fracture models with reservoir engineering data. Examples of such reservoir production data are results of measures obtained from: PTA (Pressure Transient Analysis), tracers, drilling operation events, PLT (production logs), and the like. In other embodiments, other reservoir production data can also be used for cross-checking during the validation of the fracture model (416).

FIG. 4B depicts aspects of the geomechanics fracture controller (412) in further detail in accordance with an embodiment of the disclosure. As shown in FIG. 4B, a seismic fracture detection process (420) is provided with seismic attributes (404A) obtained from seismic volume results (402). The seismic attributes (404A) may include attributes related to natural fractures detections or dislocation detections. Examples of such attributes obtained from the seismic dislocations attribute analysis results may include: variance, anti-tracking, flatness, curvature, and the like. In other embodiments, other seismic attributes may also be provided. As will be appreciated, seismic fracture attributes may be unable to be compared straight forward at wellbore scale due to resolutions issues. However, seismic attributes may be used as a seismic fracture controller or conduct for minor fractures detected at wellbore scale if the relations regarding to the locations and intensity between them exist.

As shown in FIG. 4B, advance seismic fracture detection may also be performed during the seismic fracture detection process (420) using azimuthal seismic analysis (404B) to capture the variations of the wave propagation at different directions. Such variations in wave propagation form anisotropic volumes in the reservoir layer and are helpful in detecting fractures. This azimuthal analysis may be based on whether the anisotropy response in the reservoir is due to natural fractures or caused by another reason. In order to identify whether the anisotropy response may be azimuthal shear anisotropy, sonic acoustic acquisition may be performed at a well location in the naturally fractured reservoir. An example of azimuthal seismic analysis is described in: Gray, F. D. and Head, K. J., 4000, Fracture Detection in the Manderson Field: A 3D AVAZ Case History: The Leading Edge, Vol. 19, No. 11, 1414-1421; and Khalid Al-Hawas, Mohammed Ameen, Mohammad Wahab, and Ed Nebrija, Saudi Aramco, Dhahran, Saudi Arabia Colin Macbeth, Heriot-Watt University, Edinburgh, U.K., 4003, "Delineation of Fracture Anisotropy Signatures in Wudayhi Field by azimuthal seismic data", the Leading Edge.

The geomechanics fracture controller (412) may include a determination of a 1D mechanical earth model (MEM) (422) to determine the rock mechanical properties and stress regime conditions in the reservoir layer. The determination of the 1D MEM may include computing the elastic rock mechanical properties deriving from well logs (408b) and rock mechanical test (408c); using additional information such as reservoir formation pressures (408e) and a Formation Integrity Test (FIT)) 408d), the in-situ stress regime can be predicted and mechanical stratigraphy (Geomechanical Facies) computed. The mechanical stratigraphy may conform the rock mechanical response to the geological deformation process and may be used as constraints for natural fractures presence, constraining their development to some particular layer through brittleness concepts, depending also on the deformation magnitude. Additionally, the maximum horizontal stress direction may be detected by the Borehole Image Analysis (BHI) (408a), and the in-situ stress magnitude derived from the 1D MEM may be used to predict the stress regime of a 3D geomechanics model (424) (also referred to as a "3D mechanical earth model (MEM)").

As shown in FIG. 4B, the geomechanics fracture controller (412) may include the determination of 2D/3D geomechanics forward model (426) that combines a structural model (408a) and displacement, paleo-stress, and strain measures 408b from the structural restoration model (408) with petrophysical properties (404b) from geological model (404). The results take the form of structural restoration as horizons displacement and deformation using boundary conditions. The determination of 2D/3D geomechanics forward model (426) may include as a Finite Element Method (FEM) using geomechanics numerical simulation software, to estimate the tensor stress regime corresponding to the deformation estimate from structural restoration at the in-situ stress conditions.

Figure 5:
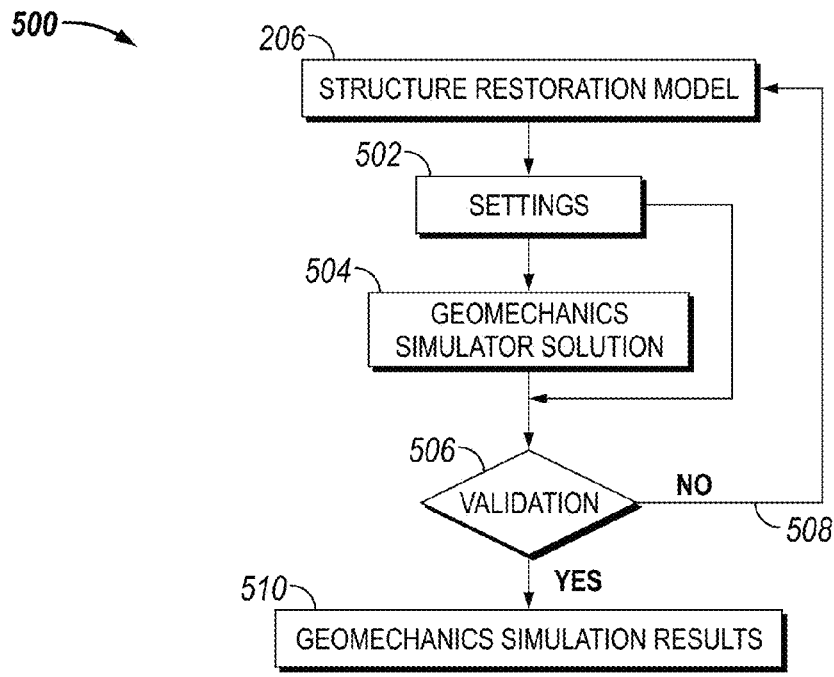
FIG. 5 is a flowchart of a process for the determination of a 2D/3D geomechanics forward model in accordance with an embodiment of the disclosure.

FIG. 5 depicts a process 500 of the determination of 2D/3D geomechanics forward model (426) in accordance with an embodiment of the disclosure. The initial parameter and strain boundary conditions may be defined for the numerical simulation and processing may be iteratively repeated until an equilibrium stress is obtained according to present to in situ stress conditions in the reservoir. As will be appreciated, a number of geomechanics simulator methodologies are commercially available and are able to estimate stress conditions using the deformation model from the structural restoration model. These results can be used to calculated or predict the possible origin for the natural fractures as stretching zones, compression zones which is an input to classify the different kind of natural fractures and their possible orientations from a qualitative perspective, using a strain tensor derivate from the 2D/3D geomechanics forward model (426). Example geomechanics simulator methodologies include ABAQUS™ from Dassault Systemes; VISAGE™ from Schlumberger; and ELFEN™ from Rockfield, COMSOL™ from AltaSim Technologies.

As shown in FIG. 5, input measures from the structural restoration modeling (406) are received for the 2D/3D geomechanics forward model (426) and stored as initial settings (502). The settings (502) are then processed by a geomechanics simulator (504) of the type described above. The output from the geomechanics simulator is then cross-checked or validated (506) against specified stress equilibrium conditions. As shown in FIG. 5, if confirmation results are not achieved during the current iteration (line 508), the previous settings of the step are adjusted for iteration by simulation step. The iterations may be repeated until specified conditions are validated. After validation, the simulation results (510) may be provided as the 2D/3D geomechanics forward model (426) and may indicate conditions of stress, strain and pre-existing faults and fractures in the reservoir layer.

The 3D geomechanics model (424) of the geomechanics fracture controller (412) may include the measures and indications of rock mechanical properties distribution. The 3D geomechanics model (424) may further include elastic rock properties and rock strength throughout the 3D geological grid. The 3D geomechanics model (424) may be calculated by boundary conditions to simulate the in-situ stress regime. As discussed in the disclosure, the in-situ stress regime is a condition where the stress field is unperturbed or is in equilibrium without any production or influences of perforated wells.

The determination of the 3D geomechanics model (424) may use elastic seismic inversion (402d) in the form of acoustic impedance, bulk density, and may also include pore pressure (402c) covering the 3D geological model area. The seismic inversion parameters may be obtained from an elastic seismic inversion (402d) and seismic velocity analysis for the pore pressure (402e). The determination of the 3D geomechanics model (424) may also be based on rock mechanical correlations between dynamics and static elastic rock mechanical properties which have been determined as a result of the 1D mechanical earth model (MEM) (422). 3D mechanical stratigraphy may also be calculated using the elastic properties of the 3D geomechanics model (424) and may be used to constrain the fracture distribution using brittleness property definition. An example processing methodology for determining the 3D geomechanics model (424) is described in: Herwanger, J. and Koutsabeloulis, N. C.: "Seismic Geomechanics—How to Build and Calibrate Geomechanical Models using 3D and 4D Seismic Data", 1 Edn., EAGE Publications b.v., Houten, 181 pp., 4011.

Additionally, geomechanics forward modeling of the type described infra and shown in FIG. 5 may be used as a loop process between the 2D/3D geomechanics forward model (426) and 3D geomechanics model (424). Such a loop process may capture the displacement and deformation quantified in the structural restoration model (406), and may provide more accurate calculations of the strain distribution corresponding to the structural evolution faulting and folding in the model (406).

The determination of the 3D geomechanics model (426) may include a geomechanics fracture indicator (428) that may form indications of fractures based on selected rock mechanical properties distributed for the 3D geomechanics model (424). The mechanical stratigraphy may be defined in the 3D geomechanics model (424) by using the Brittleness concept and may be used as a geomechanics fracture indicator to define the fracture position and density or spacing through the layering. A strain or plastic strain model may be determined in the 2D/3D geomechanics forward model (426) and 3D geomechanics model (424) and may be used as indicator of fracture orientation (dip and azimuth) and possible areal/volumetric density distribution, according to the kind of geological structural environment. Several components of fractures can be considered as geomechanics indicator for fractures, such as fractures relate to folding and fractures related to faulting. The quantifications about the strain may be qualitative in terms of real fracture density present in the reservoir.

As shown in FIG. 4B, the determination of the 3D geomechanics model (424) may include a fracture indicator controller (430). The fracture indicator controller (430) may compare attributes determined from seismic fracture detection (420) and geomechanics fracture indicator (428) in terms of fracture position, fracture density and orientation in a qualitative way, to evaluate possible coincidence zones, between the models, where natural fractures can be expected to be created. In some cases, the attributes determined from seismic fracture detection (420) and geomechanics fracture indicator (428) may be complementary due to the different vertical and areal resolution in which both of them are calculated.

The discrete fracture model (414) may be determined subsequent to identification of natural fracture locations by the fracture indicator controller (430). The discrete fracture model may build a representative natural fracture model based on stochastic mathematical simulations. As shown in FIG. 4B, the discrete fracture model (414) may be constructed from the fracture indicator controller (430) and the intensity and orientation from the 1D natural fracture characterization (418).

The determination of the discrete fracture model (414) may receive as input the results of the 1D natural fracture characterization (418), which may be obtained from the borehole image resistivity analysis or acoustic image interpretation (408a) of the core and well logs (408) and may represent the intensity fracture, aperture, fracture classification and fracture orientation along a wellbore.

As noted infra, the discrete fracture model (414) may be determined using the fracture indicator controller (430) and the 1D natural fracture characterization (418). The determination may constrain the orientation and fracture intensity in a qualitative way and using the 1D natural fracture characterization (418), may calculate the real fracture intensity quantification. This output can be used to predict a natural fracture model through the discrete fracture network methodology. For fracture intensity quantification purposes, the fracture intensity derived from the fracture indicator controller (430) may be normalized for comparison with the BHI fracture intensity derived from the 1D natural fracture characterization (418).

The fracture model validation 416 may validate the discrete fracture model (414). The validation may be performed using reservoir production data. As shown in FIG. 4B, several types of data may be used as fracture dynamic properties (432) to calibrate the fracture model with reservoir engineering measures (410). For example, results from a PTA (Pressure Transient Analysis) test, or measures from tracers, drilling operations, production logs, and the like may be used. For example, pressure transient analysis can estimate permeability contribution due to fracture presence and the capacity for fluid flow due to the fracture presence. In another example, tracer injection, production logs, interference test and possibly some drilling events as can indicate mud loss circulation that can provide evidence of the presence of natural fractures. The discrete fracture model (414) may upscale into the fine-scale cell grid geological model, and reproduce the natural fracture distribution and their properties to compare with the validation data.

After the fracture model validation, a discrete natural fracture model (434) may be produced as a result of the process 400. As previously described, the discrete natural fracture model (434) may indicate the presence and extent of natural fractures in the subsurface geological structures.

Next, fluid flow paths may be identified (block 116). The fluid flow paths may be identified using a critical stress concept based on the Mohr-Coulomb criterion. As known in the art, the Mohr-Coulomb criteria depend on the stress magnitude and orientation of the fracture planes with respect to the in-situ stress orientation. This orientation affects the normal and shear stress on the fracture plane.

Fracture networks usually serve as the major fluid-flow paths for fluid transportation within the subsurface rocks, especially if the matrix permeability is poor or has a low permeability as compared to the permeability of the fracture. The partitioning of fluid-flow within a population of fractures relies on the spatial connectivity of fracture geometry and the transmissivity of individual fractures, both of which may be affected by the geomechanical conditions.

The identification of fluid flow pathways may include determining critical fractures in the reservoir of interest may be determined. As will be appreciated, critical stress depends on the stress magnitude and the orientation of the fracture plane with respect to the in-situ stress orientation. The stress orientation affects the normal and shear stresses acting in the fracture plane. When normal and shear stress exceed the friction angle (for non-intact rock), the shearing may produce dilation that keeps the fracture hydraulically open.

Figure 6A:
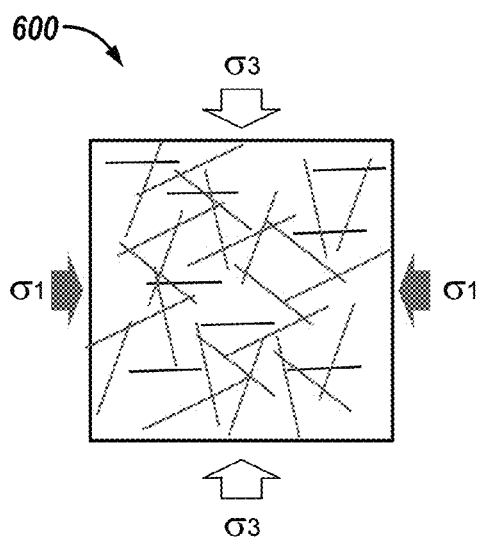
FIG. 6A is a diagram illustrating fluid flow paths for hydraulically conductive and non-hydraulically conductive fractures using normal stresses in accordance with an embodiment of the disclosure.
Figure 6B:
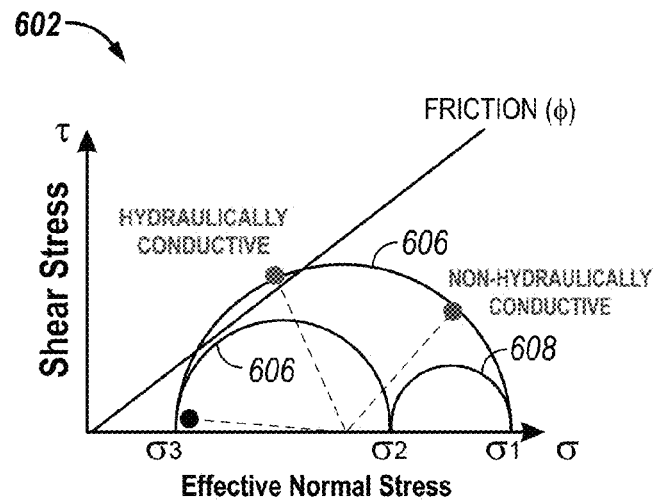
FIG. 6B is a plot of shear stress vs normal stress and coefficient of friction in accordance with an embodiment of the disclosure.

Fractures in this state may be referred to as "reactivated," "critically stressed," or as a "fluid flow path." FIG. 6A is a diagram 600 illustrating fluid flow paths for hydraulically conductive and non-hydraulically conductive fractures using normal stresses ($\sigma_1$ and $\sigma_3$) in accordance with an embodiment of the disclosure. FIG. 6B is a plot 602 of shear stress vs normal stress and coefficient of friction in accordance with an embodiment of the disclosure. FIG. 6B illustrates "Mohr circles" 604, 606, and 608, as is known in the art.

Shear failure may be caused by two perpendicular stresses acting on the same plane, and is defined in conjunction with a Mohr circle by the following equation expressing stress conditions shown schematically in FIG. 6B:

$$\sigma 1' \geq C0 + \sigma 3' \tan 2\beta \quad (1)$$

Where C0 is the unconfined compressive strength, $\sigma 1'$ is the maximum effective stress, $\sigma 3'$ is the minimum effective stress, and $\beta$ is the angle between the normal stress and the maximum effective stress $\sigma 1'$, such is $\beta$ is determined as follows:

$$\beta = 45° + \frac{\phi}{2} \quad (2)$$

Where $\phi$ is the friction angle.

If the maximum effective stress $\sigma 1'$ is exceeded, then the conditions for shear failure are satisfied.

In some embodiments, fluid flow paths may be identified according to the techniques described in U.S. patent application Ser. No. 17/476,914 filed Sep. 16, 2021, and titled "IDENTIFYING FLUID FLOW PATHS IN NATURALLY FRACTURED RESERVOIRS," a copy of which is incorporated by reference in its entirety. For example, in some embodiments normal effective stress and shear stress may be determined. In terms of stress tensor components $\sigma_{i,j}$ the normal stress may be defined as the product of stress vector multiplied by normal unit vector $\sigma_n = T^{(n)} \cdot n$ and the magnitude of the shear stress ($\tau_n$) component as defined in Equation 3:

$$\tau_n = \sqrt{(T^{(n)})^2 - \sigma_n} \quad (3)$$

A fluid flow path may be determined from shear stress and normal effective stress as shown in Equation 4:

$$\text{Fluid flow path} = (\tau - \sigma_n * \tan(\phi) \geq 0 \quad (4)$$

In some embodiments, fluid flow paths for a fracture network in a rock matrix may be identified by using determined apertures combined with the normal effective stress and shear stress. The largest aperture corresponds to the greatest distance between the points and the failure Mohr Coulomb line (that is, the friction angle for non-intact rock). In some embodiments, apertures may be determined from microresistivity logs calibrated microresistivity arrays, the fracture dataset, shallow resistivity, and drilling mud resistivity. The fracture aperture determination may be performed using Equation 5:

$$W = cAR_m^b R_{xo}^{1-b} \quad (5)$$

where W is the fracture width (that is, aperture), Rxo is the flushed zone resistivity, Rm is the mud resistivity, and A is the excess current flowing into the rock matrix through the conductive media due to the presence of the fracture. The excess current is a function of the fracture width and may be determined from statistical and geometrical analysis of the anomaly it creates as compared to background conductivity. For example, the excess current may be determined by dividing by voltage and integrating along a line perpendicular to the fracture trace. The term c is a constant and b is numerically obtained tool-specific parameter (that is, specific to the resistivity tools). As will be appreciated, a greater fracture aperture (W) indicates a more open fracture that is likely to flow hydrocarbons or other fluids, and a lesser fracture aperture indicates a fracture that will likely have reduced or low flow to hydrocarbons or other fluids.

The determined fracture aperture mean values may be provided in two forms: as sinusoids along fractures and as a secondary track with the mean value points. In addition to the mean fracture aperture, the hydraulic mean fracture aperture may be determined using Equation 6:

$$FVAH = \sqrt[3]{\frac{\sum(\text{length} \times \text{aperture}^3)}{\text{Total Length}}} \quad (6)$$

where FVAH is the hydraulic mean fracture aperture.

The fracture modeling workflow 112 also includes scaling-up the fracture model properties including porosity and permeability (block 120). In some embodiments, the scaling-up of fracture model properties may include fracture aperture. The scale-up is used to transform the fluid-flow planes into 3D grid block properties that generate fracture tensor permeability, porosity, and sigma or shape factor. In some embodiments, the conversion from discrete fracture planes to a grid model may be performed using Oda's method. In some embodiments, the conversion from discrete fracture plans to a grid model may be performed according to the techniques described in U.S. Publication No. 2020/0095858 filed Nov. 26, 2019, and titled "MODELING RESERVOIR PERMEABILITY THROUGH ESTIMATING NATURAL FRACTURE DISTRIBUTION AND PROPERTIES," a copy of which is incorporated by reference in its entirety. In such embodiments, the upscaling process may be performed using a software package such as Petrel™, Fracflow®, or other suitable upscaling methodology.

Figure 7:
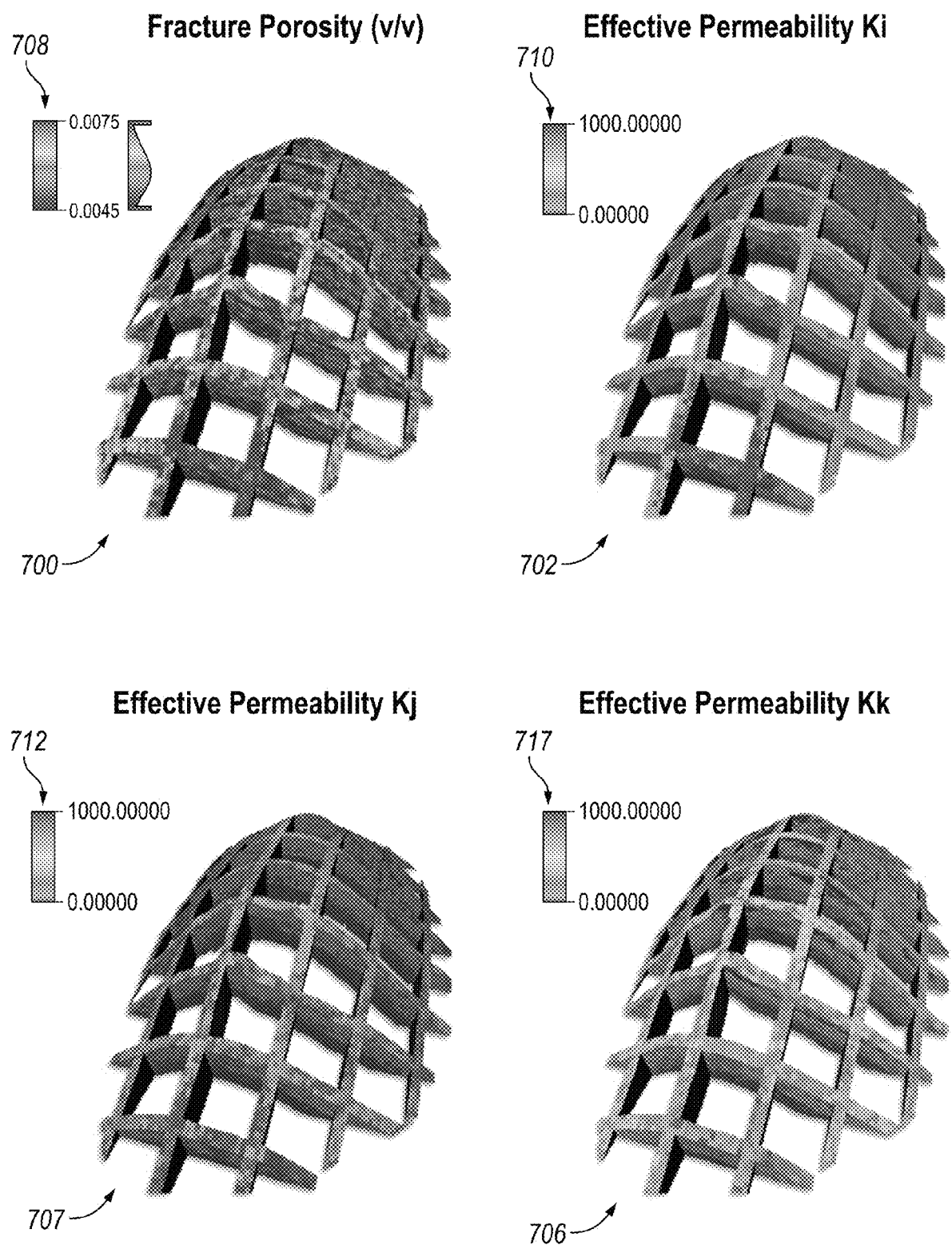
FIG. 7 depicts fracture porosity and an effective permeability tensor determined using scale-up of fracture model properties in accordance with an embodiment of the present disclosure.

By way of example, FIG. 7 depicts fracture porosity 700 and an effective permeability tensor 702, 707, and 707 determined using scale-up of fracture model properties in accordance with an embodiment of the present disclosure. FIG. 7 also includes color legends 708, 710, 712, and 717 illustrating the colors for the corresponding values of the scaled up properties. As shown in FIG. 7 the fracture porosity 702 is in units of void (pore) volume per unit bulk volume and the permeability tensor in Ki (702), Kj (707), and Kk (707).

Next, the fracture properties of the fracture model may be calibrated using the fracture properties (for example, fracture porosity and fracture permeability) derived from the X-ray MicroCT workflow (block 120). Multiple fracture realizations may be generated based on uncertainty parameters, according to the techniques described in U.S. Publication No. 2020/0095858 filed Nov. 26, 2019, and titled "MODELING RESERVOIR PERMEABILITY THROUGH ESTIMATING NATURAL FRACTURE DISTRIBUTION AND PROPERTIES, incorporated by reference in its entirety. The realizations may be determined in order to minimize the differences shown in Equation 7 as follows:

$$KH_{PTA} \approx KH_{Fract\text{-}simulate} + KH_{HPS} + KH_{Facim} \quad (7)$$

Where KHPTA is the flow capacity from pressure transient analysis (PTA), $KH_{Fract\text{-}simulate}$ is the flow capacity from the fracture model, $KH_{HPS}$ is the flow capacity for high permeability streaks (HPS), and $KH_{Facim}$ is the flow capacity from the matrix model. High permeability streaks (HPS) are typically found in a producing formation matrix. The high permeability streaks are separate from natural fractures and are features related mainly to carbonate environments. High permeability streaks correspond to intervals with high permeability due to the presence of vuggy porosity or other diagenetic features in the rock matrix. The presence of HPS intervals can be detected partially by the conventional permeability workflow for matrix using a comprehensive characterization of the rock types. However, in some cases those intervals cannot be quantified correctly due to bad borehole conditions and may thus be underestimated. In such cases, additional corrections may be provided, such as those from what is known as a $M_{HPS}$ parameter.

After calibration, the calibrated fracture model may be used to determine locations for drilling and hydraulic fracturing operations. For example, suitable intervals for hydraulic fracturing may be identified using the fracture network, and a hydraulic fracturing operation may be performed at a location in a reservoir of interest. A well may be drilled at an identified location and fracturing fluid may be pumped into the wellbore of the well to cause fracturing of reservoir rock.

Figure 8:
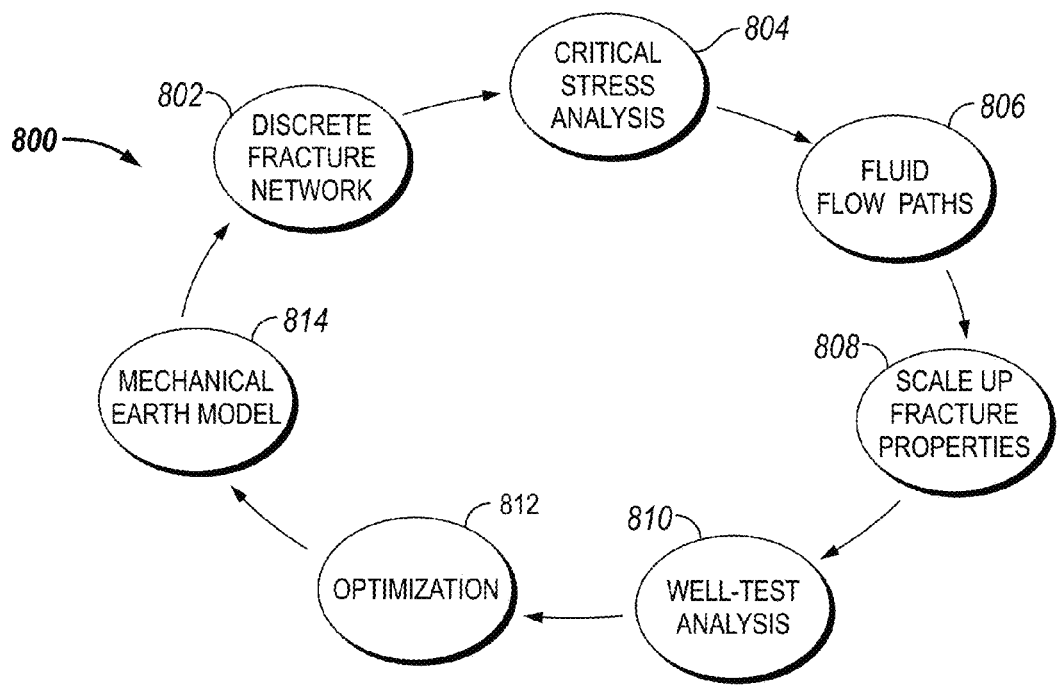
FIG. 8 is a diagram of a workflow 800 for multiple fracture realizations that may be used for validations and calibrations in accordance with an embodiment of the disclosure.

FIG. 8 depicts a workflow 800 for multiple fracture realizations that may be used for validations and calibrations in accordance with an embodiment of the disclosure. The impact of critically stressed aperture and permeability on fluid flow may be quantified using equivalent permeability, which considers fracture, HPS, and matrix flow and the interaction between these three factors. For example, FIG. 8 depicts the following determinations: discrete fracture network 802, critical stress analysis 804, fluid flow paths 806, the scale up of fracture properties 808, well test analysis 810, optimization 812, and a mechanical earth model 814. As discussed infra, the realizations may be determined according to the techniques described in U.S. Publication No. 2020/0095858 filed Nov. 26, 2019, and titled "MODELING RESERVOIR PERMEABILITY THROUGH ESTIMATING NATURAL FRACTURE DISTRIBUTION AND PROPERTIES."

Figure 9A:
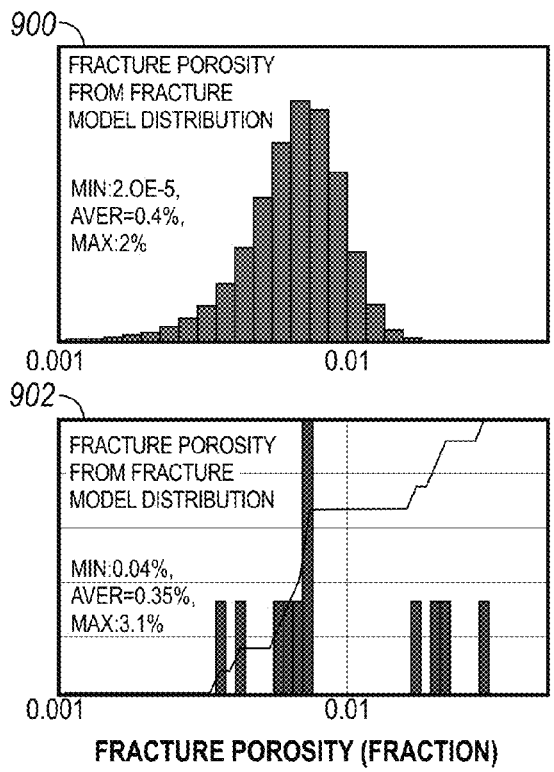
FIG. 9A depicts an example fracture porosity distribution for a fracture model upscale process and a fracture porosity obtained from X-ray MicroCT in accordance with an embodiment of the disclosure.
Figure 9B:
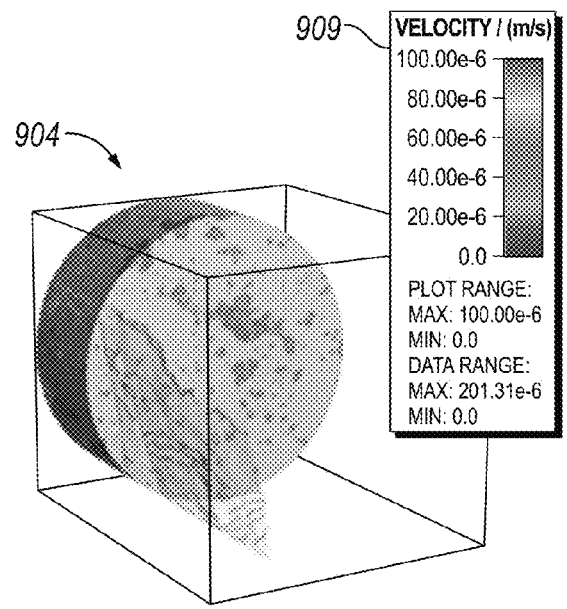
FIG. 9B depicts a velocity field for the core plug used to determine the fracture porosity depicted in FIG. 9A in accordance with an embodiment of the disclosure.

FIG. 9A depicts an example fracture porosity distribution 900 for a fracture model upscale process and a fracture porosity 902 obtained from X-ray MicroCT in accordance with an embodiment of the disclosure. FIG. 9B depicts a velocity field 904 for the core plug used to determine the fracture porosity 902 and a color legend 909 in accordance with an embodiment of the disclosure. As shown in FIG. 9A, the fracture porosity 902 obtained from X-ray MicroCT is consistent with the fracture porosity distribution 900 from the fracture model upscale process.

Figure 10A:
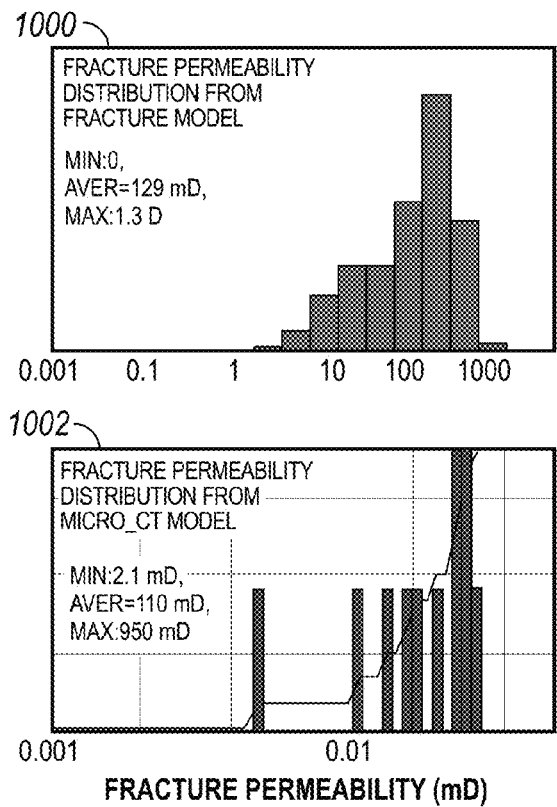
FIG. 10A depicts an example average fracture effective permeability distribution for a fracture model upscale process and a fracture effective permeability obtained from X-ray MicroCT in accordance with an embodiment of the disclosure.
Figure 10B:
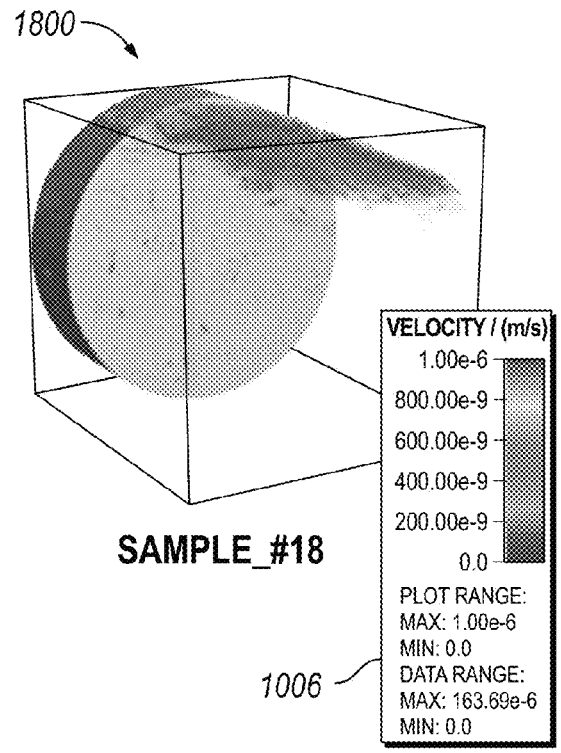
FIG. 10B depicts a velocity field for the core plug used to determine the fracture effective permeability depicted in FIG. 10A in accordance with an embodiment of the disclosure.

FIG. 10A depicts an example average fracture effective permeability distribution 1000 for a fracture model upscale process and a fracture effective permeability 1002 obtained from X-ray MicroCT in accordance with an embodiment of the disclosure. FIG. 10B depicts a velocity field 1004 for the core plug used to determine the fracture porosity 1002 and a color legend 1004 in accordance with an embodiment of the disclosure. As shown in FIG. 10A, the fracture effective permeability 1002 obtained from X-ray MicroCT is consistent with the average fracture effective permeability distribution 1000 from the fracture model upscale process.

Figure 11:
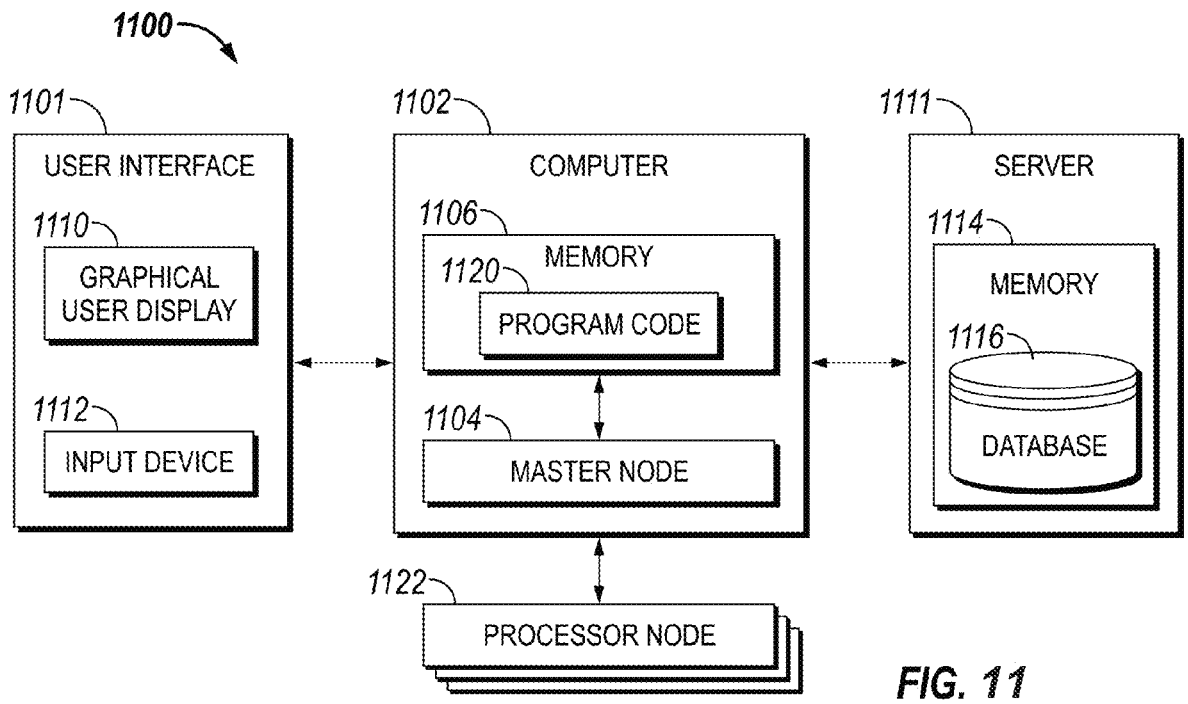
FIG. 11 is a block diagram of a data processing system in accordance with an embodiment of the disclosure.

FIG. 11 depicts a data processing system 1100 that includes a computer 1102 having a master node processor 1104 and memory 1106 coupled to the processor 1104 to store operating instructions, control information and database records therein in accordance with an embodiment of the disclosure. The data processing system 1100 may be a multicore processor with nodes such as those from Intel Corporation or Advanced Micro Devices (AMD), or an HPC Linux cluster computer. The data processing system 1100 may also be a mainframe computer of any conventional type of suitable processing capacity such as those available from International Business Machines (IBM) of Armonk, N.Y., or other source. The data processing system 1100 may in cases also be a computer of any conventional type of suitable processing capacity, such as a personal computer, laptop computer, or any other suitable processing apparatus. It should thus be understood that a number of commercially available data processing systems and types of computers may be used for this purpose The computer 1102 is accessible to operators or users through user interface 1108 and are available for displaying output data or records of processing results obtained according to the present disclosure with an output graphic user display 1110. The output display 1110 includes components such as a printer and an output display screen capable of providing printed output information or visible displays in the form of graphs, data sheets, graphical images, data plots and the like as output records or images.

The user interface 1108 of computer 1102 also includes a suitable user input device or input/output control unit 1112 to provide a user access to control or access information and database records and operate the computer 1102. Data processing system 1100 further includes a database of data stored in computer memory, which may be internal memory 1106, or an external, networked, or non-networked memory as indicated at 1114 in an associated database 1116 in a server 88.

The data processing system 1100 includes executable code 820 stored in non-transitory memory 1106 of the computer 1102. The executable code 820 according to the present disclosure is in the form of computer operable instructions causing the data processor 1104 to determine geomechanical components, determine a discrete natural fracture model, identify fluid flow paths, determine porosity and effective permeability, and calibrate a natural fracture model, according to the present disclosure in the manner set forth.

It should be noted that executable code 1120 may be in the form of microcode, programs, routines, or symbolic computer operable languages capable of providing a specific set of ordered operations controlling the functioning of the data processing system 1100 and direct its operation. The instructions of executable code 1120 may be stored in memory 1106 of the data processing system 1100, or on computer diskette, magnetic tape, conventional hard disk drive, electronic read-only memory, optical storage device, or other appropriate data storage device having a non-transitory computer readable storage medium stored thereon. Executable code 1120 may also be contained on a data storage device such as server 1111 as a non-transitory computer readable storage medium, as shown.

The data processing system 1100 may be include a single CPU, or a computer cluster as shown in FIG. 11, including computer memory and other hardware to make it possible to manipulate data and obtain output data from input data. A cluster is a collection of computers, referred to as nodes, connected via a network. A cluster may have one or two head nodes or master nodes 1104 used to synchronize the activities of the other nodes, referred to as processing nodes 1122. The processing nodes 1122 each execute the same computer program and work independently on different segments of the grid which represents the reservoir.

Ranges may be expressed in the disclosure as from about one particular value, to about another particular value, or both. When such a range is expressed, it is to be understood that another embodiment is from the one particular value, to the other particular value, or both, along with all combinations within said range.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments described in the disclosure. It is to be understood that the forms shown and described in the disclosure are to be taken as examples of embodiments. Elements and materials may be substituted for those illustrated and described in the disclosure, parts and processes may be reversed or omitted, and certain features may be utilized independently, all as would be apparent to one skilled in the art after having the benefit of this description. Changes may be made in the elements described in the disclosure without departing from the spirit and scope of the disclosure as described in the following claims. Headings used in the disclosure are for organizational purposes only and are not meant to be used to limit the scope of the description.

What is claimed is:

1. A method of drilling a well in a subsurface geological structure to a location in a subsurface hydrocarbon reservoir indicated by a natural fracture network model of the reservoir, the method comprising:
   obtaining a core plug from the subsurface geological structure;
   obtaining an image of a sample from the core plug using X-ray micro-computed tomography;
   determining, using the image, a first fracture porosity and a first fracture effective permeability of the subsurface hydrocarbon reservoir;
   obtaining reservoir parameters representing properties of the subsurface reservoir for processing in a data processing system;
   forming a natural fracture model by processing the obtained reservoir parameters to identify the presence and extent of natural fractures at locations in the subsurface hydrocarbon reservoir;
   identifying a fluid flow path using a shear stress, a normal stress, and an aperture of a fracture;
   determining a discrete natural fracture network in the natural fracture model using the fluid flow path;
   determining a second fracture porosity and a second fracture effective permeability from the nature fracture model;
   comparing the second fracture porosity to the first fracture porosity and the second fracture effective permeability to the first fracture effective permeability;
   calibrating the natural fracture model based on the comparison; and
   drilling a well in the subsurface geological structure to a location in the subsurface hydrocarbon reservoir based on the identified presence and extent of natural fractures from the natural fracture model.

2. The method of claim 1, wherein the reservoir parameters comprise seismic attributes from seismic surveys of the subsurface geological structure.

3. The method of claim 1, wherein the reservoir parameters comprise rock and mechanical properties from geological models of the subsurface geological structure.

4. The method of claim 1, wherein the reservoir parameters comprise structural restoration models of the subsurface geological structure.

5. The method of claim 1, wherein the reservoir parameters comprise rock geological characterizations of the subsurface geological structure.

6. The method of claim 1, wherein the reservoir parameters comprise reservoir engineering measures obtained from production from the subsurface hydrocarbon reservoir.

7. The method of claim 1, wherein obtaining an image of a sample from the core plug using X-ray micro-computed tomography comprises:
   obtaining a sub-sample of the sample of the core plug; and
   obtaining an image of the sub-sample at a greater resolution than the image of the sample.

8. The method of claim 1, comprising:
   determining, using the image, a fracture aperture of the subsurface hydrocarbon reservoir.

9. The method of claim 1, wherein determining a second fracture porosity and a second fracture effective permeability from the nature fracture model comprises converting a discrete fracture plane of the natural fracture model to a grid model.

10. A non-transitory computer-readable storage medium having executable code stored thereon of drilling a well in a subsurface geological structure to a location in a subsurface hydrocarbon reservoir indicated by a natural fracture network model of the reservoir, the executable code comprising a set of instructions that causes a processor to perform operations comprising:
    obtaining a core plug from the subsurface hydrocarbon reservoir;
    obtaining an image of a sample from the core plug using X-ray micro-computed tomography;
    determining, using the image, a porosity and an effective permeability of the subsurface hydrocarbon reservoir;
    obtaining reservoir parameters representing properties of the subsurface reservoir for processing in a data processing system;
    forming a natural fracture model by processing the obtained reservoir parameters to identify the presence and extent of natural fractures at locations in the subsurface hydrocarbon reservoir;
    identifying a fluid flow path using a shear stress, a normal stress, and an aperture of a fracture;
    determining a discrete natural fracture network in the natural fracture model using the fluid flow path;
    determining a second fracture porosity and a second fracture effective permeability from the nature fracture model;
    comparing the second fracture porosity to the first fracture porosity and the second fracture effective permeability to the first fracture effective permeability; and
    calibrating the natural fracture model based on the comparison.

11. The non-transitory computer-readable storage medium of claim 10, wherein the reservoir parameters comprise seismic attributes from seismic surveys of the subsurface geological structure.

12. The non-transitory computer-readable storage medium of claim 10, wherein the reservoir parameters comprise rock and mechanical properties from geological models of the subsurface geological structure.

13. The non-transitory computer-readable storage medium of claim 10, wherein the reservoir parameters comprise structural restoration models of the subsurface geological structure.

14. The non-transitory computer-readable storage medium of claim 10, wherein obtaining an image of a sample from the core plug using X-ray micro-computed tomography comprises:
   obtaining a sub-sample of the sample of the core plug; and
   obtaining an image of the sub-sample at a greater resolution than the image of the sample.

15. The non-transitory computer-readable storage medium of claim 10, comprising:
   determining, using the image, a fracture aperture of the subsurface hydrocarbon reservoir.

16. The non-transitory computer-readable storage medium of claim 10, wherein determining a second fracture porosity and a second fracture effective permeability from the nature fracture model comprises converting a discrete fracture plane of the natural fracture model to a grid model.

17. A system of drilling a well in a subsurface geological structure to a location in a subsurface hydrocarbon reservoir indicated by a natural fracture network model of the reservoir, comprising:
   a processor;
   a non-transitory computer-readable memory accessible by the processor and having executable code stored thereon, the executable code comprising a set of instructions that causes a processor to perform operations comprising:
      obtaining a core plug from the subsurface hydrocarbon reservoir;
      obtaining an image of a sample from the core plug using X-ray micro-computed tomography;
      determining, using the image, a porosity and an effective permeability of the subsurface hydrocarbon reservoir;
      obtaining reservoir parameters representing properties of the subsurface reservoir for processing in a data processing system;
      forming a natural fracture model by processing the obtained reservoir parameters to identify the presence and extent of natural fractures at locations in the subsurface hydrocarbon reservoir;
      identifying a fluid flow path using a shear stress, a normal stress, and an aperture of a fracture;
      determining a discrete natural fracture network in the natural fracture model using the fluid flow path;
      determining a second fracture porosity and a second fracture effective permeability from the nature fracture model;
      comparing the second fracture porosity to the first fracture porosity and the second fracture effective permeability to the first fracture effective permeability; and
      calibrating the natural fracture model based on the comparison.

18. The system of claim 17, wherein obtaining an image of a sample from the core plug using X-ray micro-computed tomography comprises:
   obtaining a sub-sample of the sample of the core plug; and
   obtaining an image of the sub-sample at a greater resolution than the image of the sample.

19. The system of claim 17, comprising:
   determining, using the image, a fracture aperture of the subsurface hydrocarbon reservoir.

20. The system of claim 17, wherein determining a second fracture porosity and a second fracture effective permeability from the nature fracture model comprises converting a discrete fracture plane of the natural fracture model to a grid model.

* * * * *